United States Patent [19]

Kuhrts

[11] Patent Number: 5,118,510
[45] Date of Patent: * Jun. 2, 1992

[54] NIACIN DRINK MIX FORMULATION

[75] Inventor: Eric H. Kuhrts, Santa Barbara, Calif.

[73] Assignee: Hauser-Kuhrts, Inc., Santa Barbara, Calif.

[*] Notice: The portion of the term of this patent subsequent to Oct. 23, 2007 has been disclaimed.

[21] Appl. No.: 440,656

[22] Filed: Nov. 22, 1989

Related U.S. Application Data

[63] Continuation-in-part of Ser. No. 212,715, Jun. 28, 1988, Pat. No. 4,965,252, which is a continuation-in-part of Ser. No. 440,728, Nov. 22, 1989, Pat. No. 5,023,245.

[51] Int. Cl.⁵ ................................................ A61K 9/48
[52] U.S. Cl. ..................... 424/451; 424/441; 424/498; 426/294; 426/590; 514/356; 514/782
[58] Field of Search ............ 424/441, 439, 498; 426/590, 294; 514/356, 782

[56] References Cited

U.S. PATENT DOCUMENTS

| | | | |
|---|---|---|---|
| 4,459,281 | 7/1984 | Colliopoulos | 424/35 |
| 4,557,938 | 12/1985 | Sander | 426/453 |
| 4,790,991 | 12/1988 | Shaw | 424/441 |
| 4,965,252 | 10/1990 | Kuhrts | 514/54 |

Primary Examiner—Thurman K. Page
Assistant Examiner—D. Gabrielle Phelan

[57] ABSTRACT

A readily-dispersible physiologically-effective fiber drink mix containing granules which are a blend of a mineral salt which releases a physiologically-acceptable gas upon ingestion, a physiologically-acceptable edible acid, and a gel-forming dietary fiber, and which granules are coated with a gel-forming dietary fiber, starch, or protein, are disclosed. The resulting granules can be mixed into water or juice for ingestion. They readily disperse into solution and do not immediately gel up and solidify, but become activated when they reach the acid environment of the stomach and dissolve, at which time the internally-contained acid and mineral salt cooperate to mechanically disperse the fiber in a slow and prolonged manner as it hydrates, the gas released by the mineral salt and the organic acid assisting in slow disintegration of the granules. An orally-ingestible pharmaceutically-active compound, e.g., a drug, such as niacin, may also be incorporated into the granules, thereby providing a readily-dispersible drink mix of the pharmaceutically-active compound and, in the case of niacin, providing a method and a product for effectively lowering serum cholesterol without usual niacin side effects such as flushing, itching, and the like.

64 Claims, No Drawings

1

NIACIN DRINK MIX FORMULATION

The present application is a continuation-in-part of my prior-filed copending application Ser. Nos. 212,715, filed Jun. 28, 1988, now U.S. Pat. No. 4,965,252, issued Oct. 23, 1990 and 07/440,728, filed Nov. 22, 1989, now U.S. Pat. No. 5,023,245, issued Jun. 11, 1991.

BACKGROUND OF THE INVENTION

1. Field of the Invention and Prior Art

The present invention relates to a readily-dispersible physiologically-effective fiber drink mix comprising granules consisting essentially of a blend of a mineral salt which releases a physiologically-acceptable gas upon ingestion, a physiologically-acceptable edible acid, and a gel-forming dietary fiber, which granules are coated with a gel-forming dietary fiber, starch, or protein and which may also advantageously include an orally-ingestible drug or other pharmaceutically-active compound, such as niacin, in said granules.

Guar gum (Cyamopsis Tetragonoloba), a galactomannan polysaccharide, and other gel-forming fibers such as psyllium hydrophilic mucilloid, have been recognized for some time to have a therapeutic value for lowering cholesterol and helping to regulate blood sugar. The cholesterol-lowering properties of guar gum and other mucilaginous substances were initially recognized by Fahrenbach et al. (U.S. Pat. No. 3,148,144).

Guar gum is obtained from a luguminous plant which grows to a height of three to six feet. The Guar plant bears bean-like pods, each of which contains six to nine small rounded seeds. The guar seed is typically composed of 40-46% germ, 38-45% endosperm, and 14-16% husk. Guar gum is used extensively in the food industry and is recognized as safe by the Food and Drug Administration as a food additive.

Guar gum is used in the food industry for various purposes as a food additive. Even at fairly low levels it presents certain problems, such as difficulty of dispersing the guar flour in liquids, or the formation of undissolved lumps or fish eyes of powder, which are effectively sealed from further hydration by a surface gel which prevents further solubility or dispersion.

Jenkins et al. (The Lancet, 1975, 1116 and 1977, 779) discovered that a therapeutic dose of guar gum effective for lowering serum cholesterol or regulating blood sugar required administration of fairly large quantities of guar gum per day. In fact, doses of 15 to 20 grams per day were needed to obtain statistically significant cholesterol reductions.

Stemmle et al. (EPO 0080673) describes many of the problems associated with the use of guar gum in a therapeutic dose. Of the various dosage forms, such as tablets, capsules, and a powder drink mix, problems of solubility, dispersion, hydration, and gelation are all described. With respect to a tablet dosage form, it is widely known that guar gum tablets do not dissolve properly either in vitro or in vivo. The high pressures needed to manufacture tablets compresses the guar flour together and, when these tablets are placed in a gastric simulator or a dissolution apparatus, they do not dissolve. The guar particles on the surface of the tablet hydrate to form an impenetrable gel, effectively sealing off the rest of the tablet, and preventing the dispersion of the guar. After 24 hours in a dissolution apparatus, the tablet still remains undissolved, and sits like a rock at the bottom of the apparatus. Various additives normally used as disintegrants to break up tablets, such as cross-linking or wicking agents or microcrystalline cellulose, do not solve the problem.

Day and Kuhrts (U.S. Pat. No. 4,824,672) teach the use of mineral carbonates to enhance dispersion of guar gum and other gummy fibers.

With respect to powder drink mix dosage forms, similar problems exist. The guar gum is not only extremely difficult to mix and dissolve, but what small amount does hydrate immediately forms a thick gel, which becomes impossible to drink.

Steinitz (U.S. Pat. No. 2,935,408) describes the use of a suspension agent with a gum to overcome some of the problems associated with using gums as stabilizers in the food industry. In this patent, the gum is predispersed in a non-aqueous water-free liquid matrix, thereby to condition it for further dispersal throughout an aqueous carrier. An example of an ideal suspension agent was glyceryl monostearate. This results in a slurry which can be used as a stabilizer to be added to an aqueous solution such as a gravy, salad dressing, toppings, jams, etc. This slurry would not be suitable for a pharmaceutical dosage form.

Jordan (U.S. Pat. No. 3,007,879) teaches the stabilization of guar gum solutions against viscosity change, as well as an improved method of mixing such dispersions, and maintaining a stable high viscosity over a substantial period of time. Organic acids are used to stabilize the guar gum solutions, but only after they have formed a gel.

Jackson, Jr. (U.S. Pat. No. 3,313,800) describes guar gum coprecipitation with gelatin from hydro-alcoholic media. The guar gum is dissolved in the alcohol/water solution and dried. The process is one of precipitation. This further shows that gelation of guar gum is a real problem, and many different solutions to this problem have been attempted.

Applegren (U.S. Pat. No. 4,754,027) describes coating fine particles of guar gum with water:solvent and film-forming fatty acids, film-forming polymers, and ethyl cellulose. Examples of solvents are ethanol, lower ketones such as acetone, benzene, xylene, and toluene. An example is the use of a polymer of dimethylaminoethyl-methacrylate for the film-forming agent and acetone:isopropanol (40:60) as solvent. Among the many drawbacks of his contribution are the use of pollution-causing substances which require special pollution-control devices and subject the manufacture to regulatory control; the expense of the film-forming agents and solvents, making this product very expensive; and failure to provide for a further dispersion of the fine guar particles within the granules, so that, after his film dissolves, the guar still has an impenetrable film of guar gel around the nucleus. In addition, his particle size and the texture of his particles create a gritty texture and an objectionable mouthfeel to the product and his particles have a tendency to sink to the bottom when mixed in a liquid, quite in contrast to the granules of the present invention, which do not have these shortcomings.

Nittner (U.S. Pat. No. 4,675,312) discloses agglomerating a substance such as guar gum with an agglomerating agent such as an animal or vegetable product, so that the guar is metabolized more slowly in the intestines.

Showa Sangyo (J.P. 59175436) involves inhibiting viscosity (gelation) of polysaccharides (e.g., guar gum, etc.), by treating them with high pressure or ultrasonic waves. However, this could destroy the activity of the guar gum by producing a structural change.

Heath (G.B. Patent 2,030,583) forms a granulate of guar gum by agglomeration. This produces particles which will dissolve in water, producing drinkable mixtures. Granules of guar are formed by spraying the powder with atomized water and drying. Particles of 100 to 1000 microns, with a water content of 5 to 25% by weight, are created. These granules are gritty and objectionable to consumers and it has been found that each granule must be 250 microns at a maximum or else they do not dissolve, because the outer layer of the granule gels up and seals off the inner part of the granule, much like what normally occurs with the usual guar gum in tablet or capsule form. Moreover, it is very difficult to control particle growth when spraying guar with just water. It is easier to use a carrier such as carboxymethyl cellulose, as taught herein. In addition, much less water can be used than in the spraying of guar gum particles with water.

U.S. Pat. Nos. 4,790,991, 4,747,881, and 4,818,539 describe coating dietary fibers and drugs with a preswelled hydrocolloid, wherein the substrate (drug or fiber) and the hydrocolloid are not the identical material, and wherein the substrate contains cholestyramine. The hydrocolloids are selected from the group consisting of natural and modified gums, cellulose, modified celluloses, pectin, mucillages, modified starches, etc. U.S. Pat. No. 4,747,881 in particular describes coating locust bean gum with carboxymethylcellulose (Example 1). There is no mention of the use of a mineral carbonate or bicarbonate or an edible acid or of gelatin or a caseinate as coating agents. The particles created tend to form small spheres which have a gel coating around their circumference. The hydrocolloid coating slows down the gelation of the aggregate, but each individual particle does not fully disperse or hydrate when the hydrocolloid layer dissolves and the gastric fluid comes in contact with the core material (substrate). Furthermore, the hydrocolloid is always different than the substrate or core material.

EPO 0007619 discloses the use of gelatin hydrolysates to inhibit the gelation of polysaccharide gums such as guar or locust bean gums. The gelation of the gum is inhibited by admixing or blending it with gelatin and adding an effective quantity of alkalinizer such as sodium glycinate. The preferred ratio of guar gum to gelatin, however, is 0.5:1 (Example 1, EPO 0007619), which means that there is twice as much inhibitor as guar gum. This severely limits the usefulness of that invention because guar gum must be taken in large amounts to be therapeutically effective, and one would be consuming large amounts of gelatin with it. In a daily dose of 15 grams of guar gum, one would also be consuming 30 grams or more of gelatin. This patent teaches that the inhibition of gelation is believed to occur when the polysaccharide gum is first hydrated.

"The surface of the polysaccharide gum particles rapidly hydrate and associate either by hydrogen bonding or by electrostatic forces with the inhibitor, which has dissolved already. The hydrogen bonding between polysaccharide molecules, which would otherwise cause gelation, is impeded by the presence of the inhibitor".

The inhibition is reversed when the mixture is consumed and reaches the acid environment of the stomach where there is a pH change. Other protein hydrolysates and carbohydrate derivatives are also mentioned as inhibitors, because they are susceptible to pH change. The formulation also requires an alkalinizer to adjust the pH and insure inhibition of gelation. Nowhere in this patent is mentioned the coating of guar or other gel-forming fibers with gelatin or other protein or with any other substance.

GB 2021948 discloses the coating of gums such as guar gum or locust bean gum with a layer of protein such as soya flour, gluten, or casein having a greater tendency to absorb water than the gum. The gum and the coating substance are mixed in preferably equal amounts with water to produce a dough which is dried and crushed. The resulting composition gels slowly when mixed with water. There is no mention of coating a mixture or granulate of a gel-forming dietary fiber, mineral carbonate or bicarbonate, and an edible acid, with or without a drug, with a protein such as gelatin or sodium caseinate or the like.

The present invention provides a significant improvement over all known previous attempts at producing a gel-forming dietary fiber drink mix by producing a more readily and completely dispersible and more completely bioavailable product. The present invention furthermore provides such a novel delivery system vehicle for the oral consumption of a drug, such as niacin, in a powdered drink mix dosage form. Heretofore, there has not existed a niacin drink mix which can be consumed in liquid beverage form, and which virtually eliminates the unpleasant side effects of niacin such as flushing and itching and having the skin turn bright red. The following Examples illustrate the process and composition of the present invention and will serve to demonstrate the many benefits of the invention. Insofar as the present invention provides a more readily dispersible and more completely dispersible powder drink mix of a gel-forming dietary fiber, such as guar gum or the like, and moreover insofar as it provides such a drink mix which also incorporates an orally-ingestible biologically-absorbable drug or other active pharmaceutical agent, such as niacin, it definitely fulfills a longstanding need in the art.

OBJECTS OF THE INVENTION

It is an object of the present invention to provide a readily-dispersible physiologically-effective drink mix comprising granules consisting essentially of a blend of a mineral salt which releases a physiologically-acceptable gas upon ingestion, a physiologically-acceptable edible acid, and a gel-forming dietary fiber, which granules are coated with a gel-forming dietary fiber, starch, or protein, thereby to provide a superior dietary fiber drink mix, and a method of administering gel-forming dietary fiber to a subject in need thereof by the employment of a such a drink mix. Another object of the invention is to provide such a drink mix which includes an orally-ingestible biologically-absorbable pharmaceutically-active compound, such as a drug or other therapeutic agent, in said granules and in said drink mix, and a method of administering such drug or other active pharmaceutical agent by the employment of such a drink mix. An additional object of the invention is to provide such a drink mix which incorporates niacin, thereby providing a method and means for the convenient administration of niacin for its antihypercholesterolemic effect and without unwanted side effects to a subject in need thereof. Other objects of the invention will become apparent hereinafter, and still others will be obvious to one skilled in the art as the description proceeds.

SUMMARY OF THE INVENTION

The invention, then, comprises the following aspects, inter alia, singly or in combination:

A readily-dispersible physiologically-effective fiber drink mix comprising granules consisting essentially of a blend of a mineral salt which releases a physiologically-acceptable gas upon ingestion, a physiologically-acceptable edible acid, and a gel-forming dietary fiber, said granules being coated with a gel-forming dietary fiber, starch, or protein coating, such a drink mix wherein an orally-ingestible pharmaceutically-active compound is included in said granules, such a drink mix wherein said pharmaceutically-active compound is niacin, such a drink mix wherein said gel-forming dietary fiber in said granules is guar gum, such a drink mix wherein said gel-forming dietary fiber coating is also guar gum, such a drink mix wherein said gas released is carbon dioxide, such a drink mix wherein said mineral salt is selected from carbonates and bicarbonates, such a drink mix wherein the mineral salt is calcium carbonate, magnesium carbonate, magnesium bicarbonate, sodium carbonate, sodium bicarbonate, potassium carbonate, or potassium bicarbonate, such a drink mix wherein the acid is a food-grade organic acid or phosphoric acid, such a drink mix wherein said coating is a guar-gum coating, such a drink mix wherein the gel-forming dietary fiber comprises between about 25% to about 98% by weight of the composition, such a drink mix wherein the mineral salt comprises about 1% to about 30% by weight of the composition, such a drink mix wherein the physiologically-acceptable acid comprises about 0.5% to about 10% by weight of the composition, such a drink mix wherein the coating on the granules comprises about 2% to about 25% by weight of the composition, such a drink mix wherein the coating on the granules comprises about 5% to about 10% by weight of the composition, such a drink mix wherein an orally-ingestible pharmaceutically-active compound is included in said granules and wherein the amount of the orally-ingestible pharmaceutically-active compound is about 1% to about 50% by weight of the composition, such a drink mix wherein said orally-ingestible pharmaceutically-active compound is niacin, such a drink mix wherein the gel-forming dietary fiber comprises about 25% to about 98% by weight of the composition, the physiologically-acceptable acid comprises about 0.5% to about 10% by weight of the composition, the mineral salt comprises about 1% to about 30% by weight of the composition, and the coating comprises about 2% to about 25% by weight of the composition, such a drink mix wherein the coating comprises about 5% to about 10% by weight of the composition, such a drink mix wherein the orally-ingestible pharmaceutically-active compound is present in granular form, with a cellulose coating about the granules thereof, such a drink mix wherein the niacin is present in granular form, with a cellulose coating about the granules thereof, such a drink mix wherein the coating is a combination of a carboxymethyl cellulose coating and an ethyl cellulose coating, such a drink mix wherein the coating is a combination of a carboxymethyl cellulose coating and an ethyl cellulose coating, such a drink mix wherein the acid is citric acid, such a drink mix wherein the mineral salt is a carbonate or bicarbonate, such a drink mix wherein the mineral salt is calcium carbonate, such a drink mix wherein the orally-ingestible pharmaceutically-active compound is an analgesic, an antihypercholesterolemic, a vitamin, a stimulant, an appetite suppressant, or a mineral supplement, such a drink mix wherein a dispersion of the drink-mix granules in water or another orally ingestible fluid provides an effective dosage of the orally-ingestible pharmaceutically-active compound, and such a drink mix wherein a dispersion of the drink-mix granules in water or another orally ingestible fluid provides an effective dosage of the niacin.

Moreover, a readily-dispersible fiber drink mix composition which can be mixed in water or other liquid and orally ingested, the resulting solution being effective in reducing serum cholesterol, comprising granules consisting essentially of, by weight of the composition:

a gel-forming dietary fiber in amount of about 25% to about 98% by weight of the composition, a mineral salt which releases a physiologically-acceptable gas upon ingestion, in amount of about 1% to about 30% by weight of the composition, a pharmacologically-acceptable edible acid in amount of about 0.5% to about 10% by weight of the composition, said granules being coated externally with a coating selected from the group consisting of a gel-forming fiber, an animal or vegetable protein, and a starch, said coating being present in amount of about 2% to about 25% by weight of the composition, such a composition wherein the external coating is a gel-forming fiber which is the same as the fiber present internally of the granules, such a composition wherein the coating is present in amount of about 5% to about 10% by weight of the composition, such a composition wherein a biologically absorbable drug or other active therapeutic agent is present in the granule in amount of about 1% to about 50% by weight of the composition, and such a composition wherein the drug or other therapeutic agent is niacin.

Additionally, a method for administering a gel-forming dietary fiber to a human being, comprising the step of administering the gel-forming dietary fiber to said human being in the form of a readily-dispersible physiologically-effective drink mix comprising granules consisting essentially of a blend of the gel-forming dietary fiber, a mineral salt which releases a physiologically-acceptable gas upon ingestion, and a physiologically-acceptable edible acid, said granules being coated with a gel-forming dietary fiber, starch, or protein, such a method wherein an orally-ingestible pharmaceutically-active compound is included in said granules, such a method wherein said pharmaceutically-active compound is niacin, such a method wherein said gel-forming dietary fiber in said granules is guar gum, such a method wherein said gel-forming dietary fiber coating is also guar gum, such a method wherein said gas released is carbon dioxide, such a method wherein said mineral salt is selected from carbonates and bicarbonates, such a method wherein the mineral salt is calcium carbonate, magnesium carbonate, magnesium bicarbonate, sodium carbonate, sodium bicarbonate, potassium carbonate, or potassium bicarbonate, such a method wherein the acid is a food-grade organic acid or phosphoric acid, such a method wherein said coating is a guar-gum coating, such a method wherein the gel-forming dietary fiber comprises between about 25% to about 98% by weight of the composition, such a method wherein the mineral salt comprises about 1% to about 30% by weight of the composition, such a method wherein the physiologically-acceptable acid comprises about 0.5% to about 10% by weight of the composition, such a method wherein the coating on the granules comprises about 2% to about 25% by weight of the composition, such a method wherein the coating on the granules comprises about 5% to about 10% by weight of the composition, such a method wherein an orally-ingestible pharmaceutically-active compound is included in said granules and wherein the amount of the orally-ingestible pharmaceutically-active compound is about 1% to about 50% by weight of the composition, such a method wherein said orally-ingestible pharmaceutically-active compound is niacin, such a method wherein the gel-forming dietary fiber comprises about 25% to about 98% by weight of the composition, the physiologically-acceptable acid comprises about 0.5% to about 10% by weight of the composition, the mineral salt comprises about 1% to about 30% by weight of the composition, and the coating comprises about 2% to about 25% by weight of the composition, such a method wherein the coating comprises about 5% to about 10% by weight of the composition, such a method wherein the orally-ingestible pharmaceutically-active compound is present in granular form, with a cellulose coating about the granules thereof, such a method wherein the niacin is present in granular form, with a cellulose coating about the granules thereof, such a method wherein the coating is a combination of a carboxymethyl cellulose coating and an ethyl cellulose coating, such a method wherein the coating is a combination of a carboxymethyl cellulose coating and an ethyl cellulose coating, such a method wherein the acid is citric acid, such a method wherein the mineral salt is a carbonate or bicarbonate, such a method wherein the mineral salt is calcium carbonate, such a method wherein the orally-ingestible pharmaceutically-active compound is an analgesic, an antihypercholesterolemic, a vitamin, a stimulant, an appetite suppressant, or a mineral supplement, such a method wherein a dispersion of the drink-mix granules in water or another orally ingestible fluid provides an effective dosage of the orally-ingestible pharmaceutically-active compound, and such a method wherein a dispersion of the drink-mix granules in water or another orally ingestible fluid provides an effective dosage of the niacin.

Further, a method for administering a gel-forming fiber to a human being, comprising the step of administering the gel-forming dietary fiber to said human being in the form of a fiber drink mix composition which can be mixed in water or other liquid and orally ingested, the resulting solution being effective in reducing serum cholesterol, comprising granules consisting essentially of, by weight of the composition:

a gel-forming dietary fiber in amount of about 25% to about 98% by weight of the composition, a mineral salt which releases a physiologically-acceptable gas upon ingestion, in amount of about 1% to about 30% by weight of the composition, a pharmacologically-acceptable edible acid in amount of about 0.5% to about 10% by weight of the composition, said granules being coated externally with a coating selected from the group consisting of a gel-forming fiber, an animal or vegetable protein, and a starch, said coating being present in amount of about 2% to about 25% by weight of the composition, such a method wherein the external coating is a gel-forming fiber which is the same as the fiber present internally of the granules, such a method wherein the coating is present in amount of about 5% to about 10% by weight of the composition, such a method wherein a biologically absorbable drug or other active therapeutic agent is present in the granule in amount of about 1% to about 50% by weight of the composition, and such a method wherein the drug or other therapeutic agent is niacin.

Finally, such a composition wherein the size of the granules is about 30 to about 110 mesh, preferably about 50 to about 70 mesh, and such a method wherein the size of the granules is about 30 to about 110 mesh, preferably about 50 to about 70 mesh.

The Dietary Fiber

For purposes of definition in this specification, the term "dietary fiber" is defined as "remnants of plant cells resistant to hydrolysis by the alimentary enzymes of man, the group of substances that remain in the ileum but are partly hydrolyzed by bacteria in the colon", according to JAMA 262, No. 4, 542–546 (Jul. 28, 1989) in the Council Report entitled "Dietary Fiber and Health", at page 542. This article, moreover, gives considerably information as to what constitutes a "dietary fiber" and is accordingly incorporated herein by reference.

Gel-forming dietary fibers include mucillages, plant gums, pectins or pectic substances, and lignin, all of which are endogenous compounds of plant materials which are resistant to digestion by enzymes in the monogastric stomach or small intestine. Chemically, nearly all of these plant materials are carbohydrates composed of repeating monosaccharide (sugar) units. Disaccharides have two sugar units, oligosaccharides three to twelve, and polysaccharides may contain a million or more. The water-soluble fractions of these substances form gels in the stomach and intestinal tract and are known to lower serum cholesterol.

Gums and mucillages have no common structure but are polysaccharides containing several sugars with alternating monomer structures and may or may not contain uronic acids. There are many gums found in plants and cereal grains. Guar and locust bean gums are galactomannans, whereas gum arabic is an acidic polymer of galactose and rhammose. Oat and barley contain gums, but are not practical for use in the present application because of the low percentage of active gum per weight volume. Most of the gums in the present application are effective at much lower dosages. Suitable gums include, inter alia, besides guar gum, the following: locust bean gum, acacia gum, gum arabic, xanthan gum, carregeenan gum, karaya gum, tragacanth gum, and ghatti gum.

Pectin substances or pectins are mixtures of polysaccharides of partially methylated and 1.4-D galacturonic acid units with side chains containing arabinose, galactose, xylose, and rhammose. They are contained in many fruits and vegetables as well as other plants.

Other suitable gel-forming dietary fibers include psyllium husks, algal polysaccharides, glucomannan, and agar, to name a few. Lignin is a non-carbohydrate polymer of aromatic plant alcohols comprising oxygenated phenylpropane units. As a plant matures, more lignin is produced, which acts as a sort of cement as it hardens and holds together other plant cell wall constituents. Lignin passes through the digestive tract with very little change.

As already mentioned, a recent review of dietary fiber which mentions these substances is contained in the following reference: Dietary Fiber and Health, JAMA 262: No. 4, 542-546 (1989), from the Council on Scientific Affairs, American Medical Association.

Some gel-forming fibers such as guar gum are used as binders and disintegrators for compressed tablets, but at fairly low levels. At higher levels, these gel-forming fibers and gums are known not to dissolve properly when compressed into tablets.

Various unsuccessful attempts have been made to solve the problem of improper and incomplete dissolution of guar gum tablets. EPA 0080673 describes these problems in detail, and discloses the use of 5 to 30% of highly-dispersed silica gel in guar tablets. Normally used tablet disintegrants or additives such as polyvinylpyrrolidone (crosslinking agent), sodium carboxymethyl-starch, cornstarch, microcrystalline cellulose, and so on, do not lead to satisfactory results. Hard tablets are produced which do not swell properly, and which form an impenetrable layer of gel around a powder core which may pass through the gastrointestinal tract undissolved.

U.S. Pat. No. 4,824,672 describes the use of mineral carbonates to enhance dispersion of gel-forming dietary fibers in orally-administrable pharmaceutical compositions for use in reducing serum cholesterol levels. Such compositions have proved to be very effective in use for their intended purpose, but do not provide a satisfactory matrix for providing a prolonged-release unit dosage formulation of a biologically-absorbable therapeutic agent or drug, much less an effective readily-dispersible drink mix.

The foregoing EPO 0080673 mentions the employment of citric acid with guar gum tablets. The citric acid and sweeteners were used, according to that disclosure, to improve the acceptability of the tablets if they were to be chewed. Accordingly, the citric acid was there used only to provide flavor and an aromatic quality to the product. Such formulations did not contain any mineral carbonate or bicarbonate and, moreover, when a carboxylic acid such as citric acid was employed in the compositions of that invention, "the acid is coated with 1 to 20% of a water-repellent agent based on the weight of the acid", reportedly to provide increased storage stability of the product, but hardly conducive to a readily-dispersible drink mix formulation of any type.

It is apparent that the prior art has not provided any suitable readily-dispersible powder drink mix consisting essentially of granules of a gel-forming dietary fiber such as guar gum or the like, much less such a readily-dispersible drink mix containing also an effective dose of a biologically-absorbable therapeutic agent or drug.

According to the present invention, however, excellent readily-dispersible powder drink mix formulations are provided, which consist essentially of granules of the gel-forming dietary fiber, a physiologically-acceptable edible acid, preferably a food-grade organic acid or phosphoric acid, and a mineral salt which releases a physiologically-acceptable gas upon ingestion, preferably a mineral carbonate or bicarbonate which releases carbon dioxide upon ingestion, the said granules being coated with a gel-forming dietary fiber, a protein of vegetable or animal origin, or a starch. As a further advantageous embodiment of the present invention, the granules incorporated into the drink mix of the invention may contain a biologically-absorbable therapeutic agent or drug, so that an effective dose of the selected biologically-absorbable therapeutic agent or drug may be conveniently ingested in the form of a readily-dispersible and palatable drink mix upon dispersion of the same in water or other orally-ingestible fluid, such as a fruit juice or the like.

The Physiologically-Acceptable Acid

As physiologically-acceptable acid may be employed any non-toxic and edible acid such as citric, malic, succinic, ascorbic, fumaric, phosphoric, tartaric, gluconic, acetic, tannic, lactic, glycollic, or the like. Food-grade organic acids are preferred and, of organic food-grade acids, citric, tartaric, and malic are preferred due to their introduction of a definite citrous, grape, and apple flavor into the composition, respectively.

The Gel-Forming Dietary Fiber

According to the invention, any of the foregoing enumerated gel-forming dietary fibers may be employed, with gums such as guar gum and the like and psyllium seed husks in powdered form being preferred, but pectin or a pectic substance, algal polysaccharides, glucomannan, agar, lignin, or the like, or combinations thereof, may generally be employed with essentially the same results.

The Mineral Salt

According to the invention, any mineral salt which releases a physiologically-acceptable gas upon ingestion may be employed. Such gas released is preferably carbon dioxide and the mineral salt is preferably a mineral carbonate or bicarbonate, with calcium carbonate, magnesium carbonate, magnesium bicarbonate, sodium carbonate, and sodium bicarbonate, as well as the corresponding potassium carbonate and bicarbonate, being preferred.

The Coating

The gel-forming fiber, protein, or starch coating agents employed according to the present invention may be selected from among any of the following gel-forming dietary fibers previously enumerated, gelatin, casein, soy, whey, egg, and any of various starches and modified starches.

The Particle Size of the Finished Product Granules

The granules of which the readily-dispersible powder drink mix of the invention consist are advantageously screened to a particle size range of about 30 to about 100 mesh, usually about 40 to 100 mesh, preferably about 50 to 70 mesh, and are most preferably sized to pass a 60-mesh screen (U.S. Standard).

Ranges of Ingredients

According to the invention, the range for the gel-forming dietary fiber in the drink-mix granules is about 25% to 98% by weight of the composition, the range of physiologically-acceptable edible acid is about 0.5% to about 10% by weight of the composition, the range for the mineral salt is about 1% to about 30% by weight of the composition, and the weight of the gel-forming fiber, animal or vegetable protein, or starch coating on the particles is about 2% to about 25% by weight of the composition, preferably about 5% to 10% by weight of the finished product. When a drug is present in the granules of the powdered drink mix, it may conveniently be present in an amount of about 1% to about 50% by weight of the finished product. The gel-forming fiber, when employed as coating, is preferably the same fiber as employed as an essential part of the matrix of the granules themselves.

THE INVENTION

It has now been discovered that readily-dispersible drink mix granules which can be mixed in water or other liquid and orally ingested and which may optionally contain a drug, vitamin, dietary food supplement, or other active therapeutic agent, and which provide a unique, readily-dispersible, and advantageous drink-mix delivery system, can be provided which consist essentially of a gel-forming fiber, especially guar gum, a physiologically-acceptable edible acid, and a mineral salt which releases a physiologically-acceptable gas upon ingestion, the individual particles being coated with an outer coating consisting essentially of a gel-forming fiber, an animal or vegetable protein, or a starch. When mixed in water or other orally-ingestible liquid, the powdered drink mix is readily dispersed and, upon ingestion, the outer coating of the particles is weakened or removed by the action of the acid of the gastrointestinal tract, which activates the interior of the individual granules, which dissolves slowly, with the internally-contained acid and mineral salt cooperating to mechanically disperse the fiber in a slow and prolonged manner as it hydrates, the gas released by the mineral salt and organic or other acid assisting in the slow disintegration of the granules while the granules are in the gastrointestinal tract, the gas penetrating and modulating the film of the gel produced from the gel-forming dietary fiber contained within the individual granules and thus assisting in the proper disintegration of the granules and the proper dissolution of all of the drug or other therapeutic agent when present in the formulation of the invention. In addition to the external coating on the individual particles, it is the combined action of the physiologically-acceptable edible acid and the mineral salt which releases the physiologically-acceptable gas upon ingestion which cooperatively provides the advantageous characteristics to the formulations of the present invention. The present invention preferably employs a mineral carbonate or bicarbonate, and a physiologically-acceptable food-grade organic acid or phosphoric acid which, as previously set forth, are essential for the proper disintegration of the individual particles and dissolution of the granules within the intestinal tract.

Drugs or Therapeutic Agents

Among drugs or therapeutic agents which may be incorporated according to this invention, but to which it should not be limited, are:

a. Antipyretics and analgesics such as acetaminophen, aspirin and ibuprofen
b. Appetite suppressants such as phenylpropanolamine hydrochloride and stimulants such as caffeine
c. Potassium, KCl, or another mineral supplement
d. Vitamin C
e. Vitamin B-12
f. Antihypercholesterolemics, and especially Niacin
g. Antitussives, such as dextromethorphan, dextromethorphan hydrobromide, noscapine, carbetapentane citrate, and chlophedianol hydrochloride.
h. Antihistamines, such as chlorpheniramine maleate, phenindamine tartrate, pyrilamine maleate, doxylamine succinate, and phenyltoloxamine citrate.
i. Decongestants, such as phenylephrine hydrochloride, phenylpropanolamine hydrochloride, pseudoephedrine hydrochloride, and ephedrine.

Preferred particular drugs, minerals, or vitamins for which the present delivery system is ideally suited include:

Niacin, Vitamin B-12, Potassium Chloride, Vitamin C, Aspirin, Caffeine, Phenylpropanolamine hydrochloride, Ibuprofen, Pseudoephedrine, Nitroglycerin, and Gemfibrozil.

The active ingredient can be any type of medication which acts systemically and which can be administered orally to transmit the active therapeutic agent into the gastrointestinal tract and into the bloodstream in therapeutically-effective levels without early excessive peak concentrations, without being inactivated by physiological fluids, and without passing unchanged through the body of the patient or subject by being excreted unabsorbed.

The Granulation Procedure

The granules employed according to the present invention are prepared according to standard granulation procedure, as evidenced by the Examples hereof. When a drug or other active therapeutic agent is to be included in the composition, and it is desired that it be released relatively slowly, it is frequently advantageous to pulverize the drug or other therapeutic agent and to coat the particles thereof prior to formulation into a granule with the other essential ingredients of the granules according to the present invention. Suitable coatings may include, for example, sodiumcarboxymethylcellulose and, if desired, a second coating of the drug or other active ingredient particles may be effected using a further cellulose derivative such as ethylcellulose, also as evidenced according to the Examples hereof. When the particles are formed into granules according to normal granulation procedure, either wet or dry procedure as desired, taking into consideration the ingredients involved, they should be screened to provide granules having a particle size between about 30 and 110 mesh, preferably 50 to 70 mesh, and most preferably about 60 mesh, so that the coating thereof with the necessary exterior coating material will provide particles of suitable dimensions for rapid dispersibility in water or other orally-ingestible liquid. Coating of the granules with the powdered gel-forming fiber, animal or vegetable protein, or starch, which is the final step in the preparation thereof, may be readily effected using a fluid-bed granulator or other apparatus of the type which rapidly and conveniently forms a film over the exterior surfaces of the granules. Of course, such fluid-bed granulator may also be used in the first step, that of coating the drug or other active principle particles, when such are to be included in the composition.

DETAILED DESCRIPTION OF PREFERRED EMBODIMENTS

The following examples are given to illustrate the present invention, but are not to be construed as limiting.

Example 1 Niacin-Fiber Drink Mix

A niacin granulate is produced in a fluid-bed granulator (Glatt Air Techniques, Ramsey, N.J.). The niacin is sprayed with Surelease TM (Colorcon, West Point, Pa.), an ethyl cellulose preparation, to a 10% level. The resulting granulate is 90% niacin with the 10% Surelease TM coating. The granules are screened to a 60 mesh size, and are blended with the following ingredients in the same fluid-bed granulator:

| | |
|---|---|
| Guar gum | 74.35% |
| Calcium Carbonate | 10.00% |
| Citric Acid | 5.00% |
| Niacin Granulate (90%) | 6.8% |
| Orange Flavor | 3.00% |
| Aspartame | .50% |
| Beta Carotene | .35% |

The foregoing ingredients are blended thoroughly in the fluid-bed granulator with air, and are spray dried with a 10% coating of 225 bloom gelatin dispersed in water, the final percentage of the gelatin coating being between about 2% and 25% by weight, preferably 5% to 10% by weight, and in this particular case about 7.5% by weight of the finished granules. The resulting granules are again screened to a 60 mesh size.

These granules can be mixed in water or other beverage at a dose of 1 teaspoon or 5 grams, to give an extremely effective antihypercholesterolemic dose of the niacin, without the guar fiber gelling up and solidifying. Furthermore, the niacin is not immediately released in the water so that it does not go directly into the bloodstream resulting in the typical niacin side effects of cutaneous flushing, itching, and general irritation. When the instant drink mix reaches the acid environment of the stomach or, when left long enough in solution, the gelatin dissolves, releasing the gel-forming fiber, calcium carbonate, citric acid and niacin through the production of carbon dioxide. The release of niacin is further slowed down by the coating of Surelease TM, so that there is a second-stage gradual release of the niacin after the fiber has been properly dispersed by the mineral carbonate and the food-grade acid.

In further embodiments, the same composition is coated with guar gum, pectin, or with sodium caseinate (10%) instead of gelatin in the same manner and to the same extent with similar results.

Clinical Evaluation

A clinical study was conducted with the gelatin-coated formulation of Example 1 to determine its effectiveness in cholesterol reduction. Following is a summary of the results:

Twenty-four healthy subjects (10 women, 14 men; ages 33–61 years) with moderate to severe diet-resistant hypercholesterolemia (ranges; total cholesterol 246–334 mg/dl) were randomly assigned, either to the formulation of Example 1 (6 grams t.i.d.) or to a placebo treatment, for a four week period. All subjects had been following a Step 1 AHA diet. None had endocrine, hepatic, or renal disorders. Results: (mean±S.D.; N.S.-not significant)

| | 0 weeks | 4 weeks | p |
|---|---|---|---|
| NIACIN/FIBER DRINK | | | |
| Tot. Chol. | 298 ± 21 | 242 ± 29 | <0.001 |
| LDL. Chol. | 216 ± 23 | 162 ± 26 | <0.001 |
| HDL. Chol. | 52 ± 8 | 58 ± 13 | −0.130 |
| Total/HDL-Chol. | 5.8 ± 1.2 | 4.3 ± 1.0 | <0.001 |
| Total trig. | 149 ± 62 | 111 ± 36 | −0.103 |
| PLACEBO | | | |
| | 291 ± 24 | 289 ± 47 | N.S. |
| | 214 ± 16 | 216 ± 46 | N.S. |
| | 48 ± 7 | 45 ± 9 | N.S. |
| | 6.2 ± 1.9 | 6.6 ± 1.9 | N.S. |
| | 133 ± 88 | 137 ± 98 | N.S. |

There were no significant changes in routine chemistry tests.

Conclusion: The Guar-Niacin preparation of Example 1 led to a 25% reduction in LDL-cholesterol and a significant reduction in total HDL-cholesterol.

Other fibers, mineral salts, and acids may obviously replace those employed in the foregoing Example with or without the added presence of a pharmaceutically-active compound such as aspirin, Vitamin C, niacin, or the like, to provide an effective dose of the selected compound for its intended physiological effect.

EXAMPLE 2 FIBER DRINK MIX

Guar Gum (100 mesh) is blended in a fluid-bed granulator (Glatt Air Techniques, Ramsey, N.J.) with calcium carbonate and citric acid. The resulting blend was composed as follows:

| | |
|---|---|
| Guar Gum | 80% |
| Calcium Carbonate | 15% |
| Citric Acid powder (60–200 mesh) | 5% |

The above blend is then spray dried with a coating of guar gum at a 0.5% level dissolved in water. The resulting granules were screened to 60 mesh and, when stirred in water, dispersed well and did not immediately gel up. The calcium carbonate and citric acid helped to disperse the guar gum once the granules began dissolving, the calcium carbonate by the release of carbon dioxide in the acid environment of the stomach. Other fibers, mineral salts, and acids may obviously replace those employed in the foregoing Example with or without the added presence of a pharmaceutically-active compound such as aspirin, Vitamin C, niacin, or the like, to provide an effective dose of the selected compound for its intended physiological effect.

EXAMPLE 3 NUTRITIONAL DRINK MIX WITH FIBER

A nutritious drink mix was made according to the present invention. The following ingredients were added to a Glatt fluid bed granulator and blended with air:

Roche Vitamin and Mineral Premix (Roche Vitamins and Fine Chemicals, Nutley, N.J., containing the USRDA of all vitamins and minerals), guar gum (100 mesh), calcium carbonate, citric acid, L-selenomethionine, beta-carotene, and aspartame. The ingredients were measured on a weight percentage basis to yield the following dose:

| Each Dose Contains | |
| --- | --- |
| Roche Vitamin and Mineral Premix | 330 mg |
| Guar Gum | 3.4 g |
| Calcium Carbonate | 200 mg |
| Citric Acid | 150 mg |
| L-Selenomethionine | 200 mcg |
| Beta Carotene | 25,000 I.U. |

The foregoing blend is then sprayed with a coating of sodium caseinate at a 10% level, the weight percent of the coating being about 10% of the composition, dried, and blended with orange flavor and aspartame. The granules have locked-in nutrition which is protected from oxidation and light by the sodium caseinate coating. The composition also delivers a dispersed fiber when it dissolves in the stomach. As in the previous Examples, the granules can be mixed in water without immediately dissolving and gelling. When they reach the acid environment of the stomach, the coating dissolves and the nutritional components and fiber are released and dispersed in a gradual manner like food, by the action of the citric acid in combination with the carbon dioxide released by the calcium carbonate.

Other fibers, mineral salts, and acids may obviously replace those employed in the foregoing Example with or without the added presence of a pharmaceutically-active compound such as aspirin, Vitamin C, niacin, or the like, to provide an effective dose of the selected compound for its intended physiological effect.

Additional Examples

Additional Examples too numerous to enumerate may be substituted for those of the foregoing, involving only variations in the gel-forming fiber employed, the pharmacologically-acceptable edible acid, the mineral salt, and the orally-ingestible biologically-absorbable drug or other pharmaceutically- or therapeutically-active compound or principle, when present, employing any of those mentioned herein in the ranges specified, as will immediately be apparent to one skilled in the art.

It is therefore seen that the present invention provides a readily-dispersible gel-forming dietary fiber drink mix comprising as essential ingredients a gel-forming dietary fiber such as guar gum, a pharmacologically-acceptable edible acid, a pharmaceutically-acceptable gas-forming mineral salt, all blended together into granules and coated with an animal or vegetable or synthetic protein, starch, or the same or different gel-forming dietary fiber, which is far superior to any such delivery system previously available, and a method of administering a dietary fiber, with or without contained drug or other pharmaceutically-active compound, by employment of such an oral pharmaceutical or dietary composition, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A readily-dispersible physiologically-effective drink mix composition which can be made into a drinkable dispersion by admixture with water or another orally-ingestible liquid comprising granules consisting essentially of a blend of a mineral salt which releases a physiologically-acceptable gas upon ingestion, a physiologically-acceptable edible acid, and a gel-forming dietary fiber, said granules being coated with a gel-forming dietary fiber, starch, or protein coating, wherein an orally-ingestible pharmaceutically-active compound is included in said granules.

2. The drink mix of claim 1, wherein said pharmaceutically-active compound is niacin.

3. The drink mix of claim 1, wherein said gel-forming dietary fiber in said granules is guar gum.

4. The drink mix of claim 3, wherein said gel-forming dietary fiber coating is also guar gum.

5. The drink mix of claim 1, wherein said gas released is carbon dioxide.

6. The drink mix of claim 1, wherein said mineral salt is selected from carbonates and bicarbonates.

7. The drink mix of claim 6, wherein the mineral salt is calcium carbonate, magnesium carbonate, magnesium bicarbonate, sodium carbonate, sodium bicarbonate, potassium carbonate, or potassium bicarbonate.

8. The drink mix of claim 7, wherein the acid is a food-grade organic acid or phosphoric acid.

9. The drink mix of claim 8, wherein said coating is a guar-gum coating.

10. The drink mix of claim 1, wherein the gel-forming dietary fiber comprises between about 25% to about 98% by weight of the composition.

11. The drink mix of claim 1, wherein the mineral salt comprises about 1% to about 30% by weight of the composition.

12. The drink mix of claim 1, wherein the physio-logically-acceptable acid comprises about 0.5% to about 10% by weight of the composition.

13. The drink mix of claim 1, wherein the coating on the granules comprises about 2% to about 25% by weight of the composition.

14. The drink mix of claim 1, wherein the coating on the granules comprises about 5% to about 10% by weight of the composition.

15. The drink mix of claim 1, wherein the amount of the orally-ingestible pharmaceutically-active compound is about 1% to about 50% by weight of the composition.

16. The drink mix of claim 15, wherein said orally-ingestible pharmaceutically-active compound is niacin.

17. The drink mix of claim 1, wherein the gel-forming dietary fiber comprises about 25% to about 98% by weight of the composition, the physiologically-acceptable acid comprises about 0.5% to about 10% by weight of the composition, the mineral salt comprises about 1% to about 30% by weight of the composition, and the coating comprises about 2% to about 25% by weight of the composition.

18. The drink mix of claim 17, wherein the coating comprises about 5% to about 10% by weight of the composition.

19. The drink mix of claim 1, with a cellulose coating about the granules thereof.

20. The drink mix of claim 2, with a cellulose coating about the granules thereof.

21. The drink mix of claim 19, wherein the coating is a combination of a carboxymethyl cellulose coating and an ethyl cellulose coating.

22. The drink mix of claim 20, wherein the coating is a combination of a carboxymethyl cellulose coating and an ethyl cellulose coating.

23. The drink mix of claim 17, wherein the acid is citric acid.

24. The drink mix of claim 17, wherein the mineral salt is a carbonate or bicarbonate.

25. The drink mix of claim 17, wherein the mineral salt is calcium carbonate.

26. The drink mix of claim 1, wherein the orally-ingestible pharmaceutically-active compound is an analgesic, an antihypercholesterolemic, a vitamin, a stimulant, an appetite suppressant, or a mineral supplement.

27. A readily-dispersible drink mix composition which can be mixed in water or other orally-ingestible liquid and orally ingested, comprising granules consisting essentially of, by weight of the composition:
    a gel-forming dietary fiber in amount of about 25% to about 98% by weight of the composition,
    a mineral salt which releases a physiologically-acceptable gas upon ingestion, in amount of about 1% to about 30% by weight of the composition,
    a pharmacologically-acceptable edible acid in amount of about 0.5% to about 10% by weight of the composition,
    said granules being coated externally with a coating selected from the group consisting of a gel-forming fiber, an animal or vegetable protein, and a starch, said coating being present in amount of about 2% to about 25% by weight of the composition, wherein an orally-ingestible biologically-absorbable drug or other active therapeutic agent is present in the granules in amount of about 1% to about 50% by weight of the composition.

28. The composition of claim 27, wherein the external coating is a gel-forming fiber which is the same as the fiber present internally of the granules.

29. The composition of claim 27, wherein the coating is present in amount of about 5% to about 10% by weight of the composition.

30. The composition of claim 27, wherein the drug or other therapeutic agent is niacin.

31. A method for administering a gel-forming dietary fiber and an orally-ingestible pharmaceutically-active compound to a human being, comprising the step of administering the gel-forming dietary fiber and compound to said human being in the form of a readily-dispersible physiologically-effective drink mix, which can be made into a drinkable dispersion by admixture with water or another orally-ingestible liquid, comprising granules consisting essentially of a blend of the gel-forming dietary fiber, a mineral salt which releases a physiologically-acceptable gas upon ingestion, and a physiologically-acceptable edible acid, said granules being coated with a gel-forming dietary fiber, starch, or protein, wherein an orally-ingestible pharmaceutically-active compound is included in said granules.

32. The method of claim 31, wherein said pharmaceutically-active compound is niacin.

33. The method of claim 32, wherein said gel-forming dietary fiber in said granules is guar gum.

34. The method of claim 33, wherein said gel-forming dietary fiber coating is also guar gum.

35. The method of claim 34, wherein said gas released is carbon dioxide.

36. The method of claim 35, wherein said mineral salt is selected from carbonates and bicarbonates.

37. The method of claim 36, wherein the mineral salt is calcium carbonate, magnesium carbonate, magnesium bicarbonate, sodium carbonate, sodium bicarbonate, potassium carbonate, or potassium bicarbonate.

38. The method of claim 37, wherein the acid is a food-grade organic acid or phosphoric acid.

39. The method of claim 38, wherein said coating is a guar-gum coating.

40. The method of claim 31, wherein the gel-forming dietary fiber comprises between about 25% to about 98% by weight of the composition.

41. The method of claim 31, wherein the mineral salt comprises about 1% to about 30% by weight of the composition.

42. The method of claim 31, wherein the physiologically-acceptable acid comprises about 0.5% to about 10% by weight of the composition.

43. The method of claim 31, wherein the coating on the granules comprises about 2% to about 25% by weight of the composition.

44. The method of claim 31, wherein the coating on the granules comprises about 5% to about 10% by weight of the composition.

45. The method of claim 31, wherein the amount of the orally-ingestible pharmaceutically-active compound is about 1% to about 50% by weight of the composition.

46. The method of claim 45, wherein said orally-ingestible pharmaceutically-active compound is niacin.

47. The method of claim 31, wherein the gel-forming dietary fiber comprises about 25% to about 98% by weight of the composition, the physiologically-acceptable acid comprises about 0.5% to about 10% by weight of the composition, the mineral salt comprises about 1% to about 30% by weight of the composition, and the coating comprises about 2% to about 25% by weight of the composition.

48. The method of claim 47, wherein the coating comprises about 5% to about 10% by weight of the composition.

49. The method of claim 31, wherein the drink mix has a cellulose coating about the granules thereof.

50. The method of claim 32, wherein the drink mix has a cellulose coating about the granules thereof.

51. The method of claim 49, wherein the coating is a combination of a carboxymethyl cellulose coating and an ethyl cellulose coating.

52. The method of claim 50, wherein the coating is a combination of a carboxymethyl cellulose coating and an ethyl cellulose coating.

53. The method of claim 47, wherein the acid is citric acid.

54. The method of claim 47, wherein the mineral salt is a carbonate or bicarbonate.

55. The method of claim 47, wherein the mineral salt is calcium carbonate.

56. The method of claim 31, wherein the orally-ingestible pharmaceutically-active compound is an analgesic, an antihypercholesterolemic, a vitamin, a stimulant, an appetite suppressant, or a mineral supplement.

57. A method for administering a gel-forming dietary fiber and an orally-ingestible pharmaceutically-active compound to a human being, comprising the step of administering the gel-forming dietary fiber and compound to said human being in the form of a fiber drink mix composition which can be mixed in water or other orally-ingestible liquid and orally ingested, the resulting solution being effective in reducing serum cholesterol, comprising granules consisting essentially of, by weight of the composition:

a gel-forming dietary fiber in amount of about 25% to about 98% by weight of the composition, a mineral salt which releases a physiologically-acceptable gas upon ingestion, in amount of about 1% to about 30% by weight of the composition, a pharmacologically-acceptable edible acid in amount of about 0.5% to about 10% by weight of the composition, said granules being coated externally with a coating selected from the group consisting of a gel-forming fiber, an animal or vegetable protein, and a starch, said coating being present in amount of about 2% to about 25% by weight of the composition, wherein an orally-ingestible biologically-absorbable drug or other active therapeutic agent is present in the granules in amount of about 1% to about 50% by weight of the composition.

58. The method of claim 57, wherein the external coating is a gel-forming fiber which is the same as the fiber present internally of the granules.

59. The method of claim 57, wherein the coating is present in amount of about 5% to about 10% by weight of the composition.

60. The method of claim 57, wherein the drug or other therapeutic agent is niacin.

61. The composition of claim 1, wherein the size of the granules is about 30 to about 110 mesh.

62. The composition of claim 27, wherein the size of the granules is about 50 to about 70 mesh.

63. The method of claim 31, wherein the size of the granules is about 30 to about 110 mesh.

64. The method of claim 57, wherein the size of the granules is about 50 to about 70 mesh.

* * * * *